| United States Patent [19]
Gleason et al.

[11] 4,350,698
[45] Sep. 21, 1982

[54] ANTIALLERGIC IMIDOSULFAMIDES

[75] Inventors: John G. Gleason, Delran, N.J.; David T. Hill, North Wales, Pa.

[73] Assignee: SmithKline Corporation, Philadelphia, Pa.

[21] Appl. No.: 305,433

[22] Filed: Sep. 25, 1981

[51] Int. Cl.³ .................. A61K 31/47; C07D 401/12
[52] U.S. Cl. .................................. 424/258; 546/140; 546/146; 546/150
[58] Field of Search .................. 546/140; 424/258

[56] References Cited
U.S. PATENT DOCUMENTS
4,315,935 2/1982 Ali ........................................ 546/140
4,321,254 3/1982 Ali ........................................ 546/140

Primary Examiner—Mary C. Lee
Assistant Examiner—James H. Turnipseed
Attorney, Agent, or Firm—Joseph F. DiPrima; Richard D. Foggio; Alan D. Lourie

[57] ABSTRACT

Imidosulfamide derivatives useful in the treatment of allergic conditions are prepared by reaction of an appropriately substituted tetrahydroisoquinoline and chlorosulfonylisocyanate in the presence of a non-nucleophilic organic base. Pharmaceutical compositions and methods of inhibiting the symptoms of an allergic response are also disclosed.

13 Claims, No Drawings

ANTIALLERGIC IMIDOSULFAMIDES

This invention relates to novel imidosulfamides which are useful as end-organ antagonists of slow reacting substance of anaphylaxis, pharmaceutical compositions and methods of inhibiting the symptoms of an allergic response. The substance, SRS-A, has been suggested to be an important mediator of anaphylaxis in human asthma. By antagonizing the effects of this or other pharmacologically active mediators at the end-organ, bronchial smooth muscle, the compounds of this invention are valuable in the treatment of allergic diseases such as asthma.

The imidosulfamide compounds of this invention are represented by the following general structural formula (I):

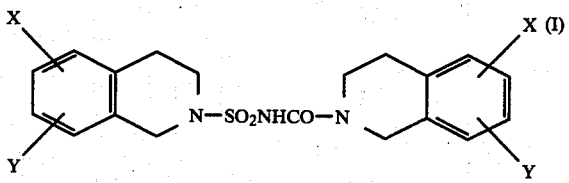

wherein X is hydrogen, bromo, chloro or methyl; and Y is bromo, chloro, methyl or 7-benzeneaminosulfonyl radical of the formula:

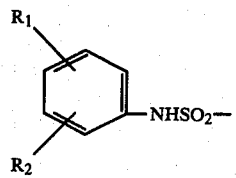

in which $R_1$ is hydrogen, bromo, chloro or methyl; and $R_2$ is bromo or chloro; and alkali metal salts of said compounds.

Particular compounds of the instant invention are compounds of the Formula (I) wherein:
 (a) X represents hydrogen and Y represents 5-bromo, 6-chloro, 7-(3-chloro-4-methylbenzeneaminosulfonyl) and 7-(3,4-dichlorobenzeneaminosulfonyl);
 (b) X represents 7-chloro and Y represents 6-chloro and 8-chloro; and
 (c) X represents 7-methyl and Y represents 8-chloro.

The compounds of the formula (I) are conveniently prepared as shown in the following scheme:

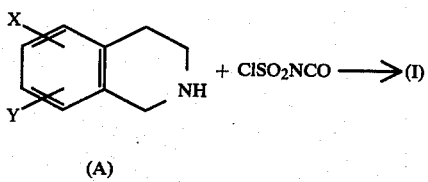

in which X and Y are as described above. Thus, the appropriately substituted tetrahydroisquinoline is reacted with chlorosulfonylisocyanate in the presence of a non-nucleophilic organic base.

Examples of such non-nucleophilic organic bases include tertiary alkylamines, such as triethylamine, tertiary alkylaryl amines, such as N,N-dimethylaniline and aromatic amines, such as pyridine.

The reaction is carried out in an inert polar organic solvent. The selection of a particular solvent is not critical provided that the solvent is substantially inert to the reagents and product. Illustrative of such a solvent is acetonitrile.

The reaction is usually carried out at moderate to low temperatures. For example, the reagents are usually mixed at temperatures of 0° C. or less and the reaction is allowed to warm gradually to ambient temperature.

The reaction time is dependent on inter alia the particular starting materials, solvent and reaction temperature. Generally, the reaction will be allowed to proceed for at least 12 hours.

The reaction product can be isolated by standard methods, for example, addition of dilute mineral acid e.g. hydrochloric acid, to the reaction mixture affords the compounds of formua (I) as the "free acid."

Alkali metal salts of the compounds of the formula (I), for example, the sodium or potassium salts, are obtainable by treatment of the compounds with the appropriate metal alkoxide, for example methoxide, in an alkanol solvent such as methanol; by treatment of the compounds with an alkali metal hydride, such as sodium hydride or potassium hydride, in a polar non-protic solvent, such as tetrahydrofuran, or dimethoxyethane; or by treatment of the compounds with a cationic exchange resin, such as a sulfonic acid resin in the sodium form.

The starting tetrahydroisoquinolines of the formula (A), wherein Y is an appropriately substituted 7-benzeneaminosulfonyl radical, are conveniently prepared by standard reactions well known in the chemical arts as shown below:

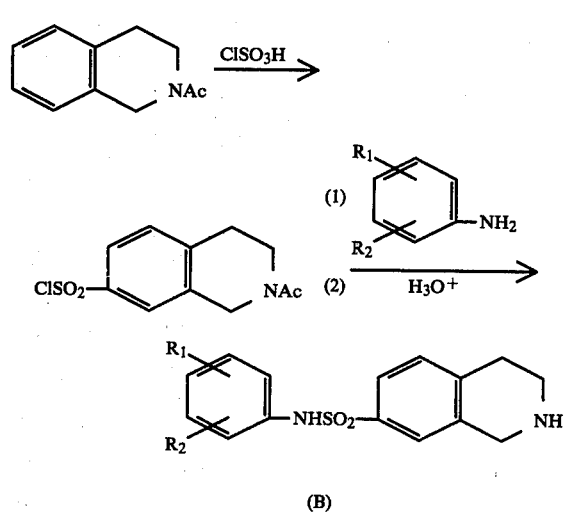

(B)

2-Acetyl-1,2,3,4-tetrahydroisoquinoline was treated with chlorosulfonic acid to yield 2-acetyl-7-chlorosulfonyl-1,2,3,4-tetrahydroisoquinoline which is then reacted with an appropriately substituted aniline followed by treatment with dilute mineral acid to give the appropriately substituted tetrahydroisoquinoline (B). The starting tetrahydroisoquinolines of the formula (A), wherein Y is not a 7-benzeneaminosulfonyl radical, are conveniently prepared by standard reactions well known to the chemical arts.

The SRS-A antagonist activity of the compounds of this invention is measured by the ability of the active medicament to inhibit SRS-A induced contraction of guinea pig ileum. In this test system, sections of ileum are resected from guinea pigs and placed in 5 ml. tissue baths containing a modified Tyrode's solution. One end of the tissue is fixed to a glass tissue holder, the other is connected to a force-displacement transducer and the tissue is placed under a tension of 500 mg. Isometric tissue contractions are recorded on a six channel polygraph. Baths are constantly aerated with 95% $O_2$-5% $CO_2$. After a 20 minute stabilization period a concentration of the appropriate agonist which provides a contraction height of 60-80% of the maximum obtainable to that agonist (as determined from full sequential concentration-response curves in separate experiments) is added to the tissue bath and the response recorded. The procedure is repeated until reproducible responses are obtained. For most agonists, two applications in rapid succession, followed 15 minutes later by a third, is sufficient to establish reproducibility. Experimental tissues are incubated with the selected concentration of the test compounds for 15 minutes. Experimental and control tissues are subjected to 5 bath changes during the incubation interval. Changes in bath fluid during the incubation period are helpful in insuring the reproducibility of tissue responses to the agonist. The same concentration of the agonist is reapplied in the presence of the test compound and the response registered and compared with controls. Percent inhibition produced by the test compound is calculated by subtracting the mean percentage change in control tissue from the mean percentage change in tissues exposed to the test compound. Additional compounds are then evaluated as long as the tissue remains reproducibly responsive to the agonist. Six tissues obtained from 6 animals are used simultaneously - 3 controls and 3 experimental.

The compounds of this invention tested at concentrations of from $5 \times 10^{-5}$ M to $1 \times 10^{-6}$ M produce marked antagonism of partially purified slow reacting substance of anaphylaxis obtained from guinea pig lung. The agonist is employed at a concentraton of 40 μg/ml.

At a compound concentration of $5 \times 10^{-6}$ M, N-(7,8-dichloro-1,2,3,4-tetrahydroisoquinoline-2yl)carbonyl-7,8-dichloro-1,2,3,4-tetrahydroisoquinoline-2-sulfonamide exhibited 46 percent antagonism.

The specificity of the antagonist activity of the compounds of this invention is demonstrated by relatively low levels of antagonism toward agonists such as potassium chloride, serotonin, and histamine.

Pharmaceutical compositions of the present invention comprise a pharmaceutical carrier or diluent and an amount of a compound of the formula (I) or an alkali metal salt thereof sufficient to produce the inhibition of the symptoms of asthma and other allergic diseases.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoro ethane and compressed carbon dioxide. Also, in addition to the pharmaceutical carrier or diluent, the instant compositions may include other ingredients such as, stabilizers, antioxidants, preservatives, lubricants, suspending agents, viscosity modifiers and the like, provided that the additional ingredients do not have a detrimental effect on the therapeutic action of the instant compositions.

The nature of the composition and the pharmaceutical carrier or diluent will of course depend upon the intended route of administration, i.e. parenterally or by inhalation.

In general, particularly for the prophylactic treatment of asthma, the compositions will be in a form suitable for administration by inhalation. Thus the compositions will comprise a suspension or solution of the active ingredient in water for adminstration by means of a conventional nebulizer. Alternatively the compositions will comprise a suspension or solution of the active ingredient in a conventional liquified propellant or compressed gas to be administered from a pressurized aerosol container. The compositions may also comprise the solid active ingredient diluted with a solid diluent for administration from a powder inhalation device. In the above compositions, the amount of carrier or diluent will vary but preferably will be the major proportion of a suspension or solution of the active ingredient. When the diluent is a solid it may be present in less, equal or greater amounts than the solid active ingredient.

For parenteral administration the pharmaceutical composition will be in the form of a sterile injectable liquid such as an ampul or an aqueous or nonaqueous liquid suspension.

Usually a compound of formula I is administered to an animal or human subject in a composition comprising an amount sufficient to produce an inhibition of the symptoms of an allergic response. When employed in this manner, the dosage of the composition is such that from 0.5 mg. to 500 mg. of active ingredient are administered at each administration. For convenience equal doses will be administered 1 to 4 times daily with the daily dosage regimen being selected from about 0.5 mg. to about 2000 mg.

The pharmaceutical preparations thus described are made following the conventional techniques of the pharmaceutical chemist as appropriate to the desired end product.

Included within the scope of this invention is the method of inhibiting the symptoms of an allergic response resulting from a mediator release which comprises administering to an animal or human subject a therapeutically effective amount for producing said inhibition of a compound of formula I, preferably in the form of a pharmaceutical composition. The adminstration may be carried out in dosage units at suitable intervals or in single doses as needed. Usually the method of this invention will be practiced when relief of allergic symptoms is specifically required, however, the method is also usefully carried out as continuous or prophylactic treatment. It is within the skill of the art to determine by routine experimentation the effective dosage to be administered from the dose range set forth above, taking into consideration such factors as the degree of severity of the allergic condition being treated, and so forth.

The following examples illustrate the preparation of compounds of formula I and their incorporation into pharmaceutical compositions and as such are not to be considered as limiting the invention set forth in the claims appended hereto.

EXAMPLE 1

Preparation of
N-(7,8-Dichloro-1,2,3,4-tetrahydroisoquinolin-2yl)Carbonyl-7,8-dichloro-1,2,3,4-tetrahydroisoquinoline-2-sulfonamide A solution of 2.0 g (0.01 mole) of 7,8-dichloro-1,2,3,4-tetrahydroisoquinoline, as the free base, in methylene chloride (10 ml) was added to a solution of chlorosulfonyl isocyanate (1 ml) in methylene chloride (10 ml) kept at 0°. The heterogeneous mixture became clear and was warmed to room temperature (precipitate formed) and allowed to stand overnight. A solution of triethylamine (1 ml) in methylene chloride (10 ml) was added, the mixture cooled to 0° and an additional 2 g (0.01 mole) of 7,8-dichloro-1,2,3,4-tetrahydroisoquinoline in methylene chloride was added. The clear solution was allowed to warm to room temperature (became yellow). After standing, a flocculent white precipitate was collected, washed (ether) and air dried (1.2 g). Recrystallization from acetonitrile gave an analytical sample (needles) m.p. 171°–173°.

| Analysis | C | H | N |
| --- | --- | --- | --- |
| Calculated: | 44.81 | 3.37 | 8.25 |
| Found: | 45.10 | 3.59 | 8.11 |

Following the procedure of Example 1, the appropriately substituted tetrahydroisoquinolines may be reacted with chlorosulfonyl isocyanate to afford the compounds in the following table:

| Cmpd No. | X | Y |
| --- | --- | --- |
| 2 | H | 5-Br |
| 3 | H | 6-Cl |
| 4 | H | 7-(3-chlorobenzeneaminosulfonyl) |
| 5 | H | 7-(3-bromobenzeneaminosulfonyl) |
| 6 | H | 7-(3-chloro-4-methylbenzeneaminosulfonyl) |
| 7 | H | 7-(3,4-dichlorobenzeneaminosulfonyl) |
| 8 | 7-Cl | 6-Cl |
| 9 | 7-$CH_3$ | 8-Cl |

EXAMPLE 2

Preparation of
7(3-chlorobenzeneaminosulfonyl)-1,2,3,4-tetrahydroisoquinoline (a) 2-acetyl-1,2,3,4-tetrahydroisoquinoline A mixture of 100 g. (0.75 mole) 1,2,3,4-tetrahydroisoquinoline and 150 ml. acetic anhydride was stirred at ambient temperature for 24 hours and then concentrated to dryness at reduced pressure. The residual liquid was dissolved in methylene chloride and solid potassium carbonate was added to neutralize the solution. The excess potassium carbonate was removed by filtration and the filtrate was concentrated to dryness at reduced pressure to afford 2-acetyl-1,2,3,4-tetrahydroisoquinoline as a yellow liquid.

(b)
2-acetyl-7-chlorosulfonyl-1,2,3,4-tetrahydroisoquinoline

To a solution of 140 g. (0.8 mole) 1,2,3,4-tetrahydroisoquinoline in 150 ml. dry methylene chloride at −15° C. with sufficient stirring was added dropwise 300 ml. (4.5 mole) chlorosulfonic acid. After the addition of the chlorosulfonic acid was complete, the reaction mixture was stirred for one hour at −15° C. and then heated to reflux for 2 hours. The reaction mixture was then cooled to 10° C. and then cautiously poured onto 3 l. of ice. The crude reaction product was then extracted in methylene chloride (2×150 ml.), dried over anhydrous magnesium sulfate and filtered. The filtrate was concentrated to dryness at reduced pressure to afford 2-acetyl-7-chloro-sulfonyl-1,2,3,4-tetrahydroisoquinoline as a viscous yellow oil.

(c)
2-acetyl-7-(3-chlorobenzeneaminosulfonyl)-1,2,3,4-tetrahydroisoquinoline

A mixture of 102 g. (0.37 mole) 2-acetyl-7-chlorosulfonyl-1,2,3,4-tetrahydroisoquinoline, 47.6 g. (0.37 mole) 3-chloroaniline, 94.0 g. triethylamine and 420 ml. dry acetone was refluxed for 4.5 hours. The reaction mixture was concentrated under reduced pressure to give a residual oil. The residual oil was dissolved in methylene chloride, washed with dilute hydrochloric acid and then with water. The methylene chloride solution was then extracted with 10% aqueous sodium hydroxide and water. The combined sodium hydroxide and water was washed with diethyl ether and then acidified with 3 N hydrochloric acid to afford the crude product as a gummy solid. The crude product was triturated with isopropanol to yield 2-acetyl-7-(3-chlorobenzeneaminosulfonyl)-1,2,3,4-tetrahydroisoquinoline with a melting point of 150°-2° C.

(d)
7-(3-chlorobenzeneaminosulfonyl)-1,2,3,4-tetrahydroquinoline, hydrochloride

A mixture of 43.3 g (0.118 mole) 2-acetyl-7-(3-chlorobenzeneaminosulfonyl)-1,2,3,4-tetrahydroisoquinoline, 575 ml. 3 N hydrochloric acid and 60 ml. n-butanol was refluxed for 3 hours. The mixture was concentrated under reduced pressure. The residue was treated with warm isopropanol to afford 7-(3-chlorobenzeneaminosulfonyl)-1,2,3,4-tetrahydroquinoline hydrochloride as an off-white solid with a melting point of 215°-17° C.

The following 7-benzeneaminosulfonyl tetrahydroisoquinolines (B) were prepared by reacting the appropriately substituted aniline with 7-chlorosulfonyl tetrahydroisoquinoline.

| Compounds of the formula B | $R_1$ | $R_2$ | Mp |
| --- | --- | --- | --- |
| B-2 | H | 3-Br | 222–225° C. (HCl) |
| B-3 | 3-Cl | 4-$CH_3$ | 257–257.5° C. (HCl) |
| B-4 | 3-Cl | 4-Cl | 251–255° C. (HCl) |

EXAMPLE 3

Preparation of the Sodium Salt of Compound 1

A solution of N-(7,8-dichloro-1,2,3,4-tetrahydroisoquinoline-2-yl)carbonyl-7,8-dichloro-1,2,3,4-tetrahydroisoquinoline-2-sulfonamide in methanol is passed through an ion exchange column (IR 120-sulfonic acid type in the sodium form) and the column eluted with methanol. The eluant is concentrated to near dryness and the resultant material is triturated with diethyl ether which after filtration under nitrogen affords the desired salt.

Similarly, alkali metal salts of the compounds of the present invention may be prepared.

EXAMPLE 4

As a specific embodiment of a composition of this invention an active ingredient, such as N-(7,8-dichloro-1,2,3,4-tetrahydroisoquinolin-2yl)carbonyl-7,8-dichloro-1,2,3,4-tetrahydroisoquinoline-2-sulfonamide, is dissolved in sterile water at a concentration of 0.5% and aerosolized from a nebulizer operating at an air flow adjusted to deliver the desired aerosolized weight of drug.

What is claimed is:

1. A compound of the formula (I)

wherein X is hydrogen, bromo, chloro, or methyl; and Y is bromo, chloro, methyl or 7-benzeneaminosulfonyl radical of the formula in which $R_1$ is hydrogen, bromo, chloro or methyl and $R_2$ is bromo or chloro; or an alkali metal salt of said compound.

2. A compound according to claim 1 wherein X is hydrogen, bromo, chloro or methyl and Y is bromo, chloro or methyl.

3. A compound according to claim 2 wherein X is hydrogen and Y is 5-bromo or 6-chloro.

4. A compound according to claim 2 wherein X is 7-chloro and Y is 6-chloro or 8-chloro.

5. A compound according to claim 2 which is N-(7,8-dichloro-1,2,3,4-tetrahydroisoquinolin-2yl)-carbonyl-7,8-dichloro-1,2,3,4-tetrahydrosioquinoline-2-sulfonamide or an alkali metal salt of said compound.

6. A compound according to claim 2 wherein X is 7-methyl and Y is 8-chloro.

7. A compound according to claim 1 wherein X is hydrogen and Y is a 7-benzeneaminosulfonyl radical of the formula which $R_1$ is hydrogen, bromo, chloro or methyl and $R_2$ is bromo or chloro; or an alkali metal salt of said compound.

8. A compound according to claim 7 wherein R is hydrogen and $R_2$ is 3-chloro or 3-bromo.

9. A pharmaceutical composition for inhibiting the symptoms of asthma comprising a pharmaceutical carrier or diluent and an amount sufficient to produce said inhibition of a compound of claim 1.

10. A pharmaceutical composition according to claim 9 in a form suitable for administration by inhalation.

11. A pharmaceutical composition according to claim 9 comprising a solution or suspension of the active ingredient in sterile water.

12. A pharmaceutical composition according to claim 9 in the form of an aerosol formulation.

13. A pharmaceutical composition according to claim 9 in which the pharmaceutical carrier or diluent is a solid.

* * * * *